United States Patent [19]

Leleu et al.

[11] Patent Number: 4,877,889

[45] Date of Patent: Oct. 31, 1989

[54] METHOD AND INSTALLATION FOR THE CRYSTALLIZATION OF GLUCONODELTALACTONE

[75] Inventors: Jean-Bernard Leleu; Patrick LeMay, both of Lestrem, France

[73] Assignee: Roquette Freres, Lestrem, France

[21] Appl. No.: 241,381

[22] Filed: Sep. 6, 1988

Related U.S. Application Data

[63] Continuation of Ser. No. 863,144, May 14, 1986, abandoned.

[30] Foreign Application Priority Data

May 15, 1985 [FR] France ................................. 85 07433

[51] Int. Cl.⁴ .......................................... C07D 309/30
[52] U.S. Cl. .................................................... 549/292
[58] Field of Search ......................................... 549/292

[56] References Cited

FOREIGN PATENT DOCUMENTS 2552777  4/1985  France .

OTHER PUBLICATIONS

"Chemical Abstracts", vol. 85, No. 1, Jul. 5, 1976, p. 488, No. 6008k, Columbus, Ohio Primary Examiner—Richard L. Raymond
Assistant Examiner—Mark W. Russell
Attorney, Agent, or Firm—Larson and Taylor

[57] ABSTRACT

A gluconic acid syrup is introduced into a first crystallization zone $1a$ which it is brought to traverse under stirring and inside which it is maintained at a constant temperature, the mixture syrup and the gluconodeltalactone crystals emerging from this first zone being brought to traverse a second crystallization zone $1b$ within which it is subjected firstly to a temperature gradient decreasing globally, possibly modulated then to a substantially constant temperature, the mixture emerging from this second zone being in the form of a crystalline mass rich in gluconodeltalactone crystals from which the latter are recovered.

34 Claims, 1 Drawing Sheet

U.S. Patent  Oct. 31, 1989  4,877,889
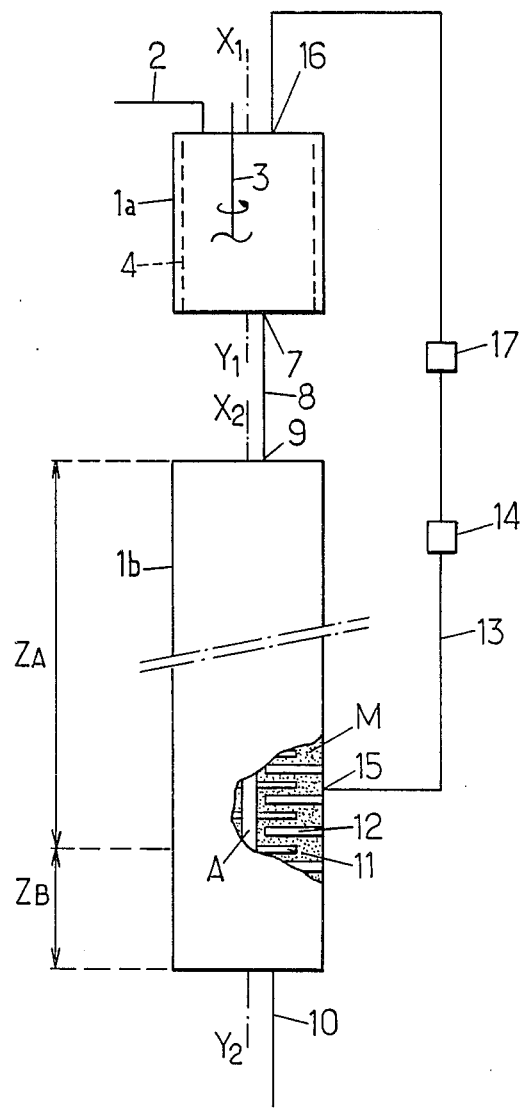

METHOD AND INSTALLATION FOR THE CRYSTALLIZATION OF GLUCONODELTALACTONE

This application is a continuation of application Ser. No. 863,144 now abandoned filed May 14, 1986.

The invention relates to a method and installation for crystallization of gluconodeltalactone or GDL.

It is known, particularly through U.S. Pat. No. 2,102,380, to prepare crystalline gluconodeltalactone from aqueous solutions rich in gluconic acid in the presence of crystals of GDL which play the role of crystallization seeds.

It is also known, through Japanese patent application published No. 49-29312 of 13 Mar. 1974 in the name of DAI ICHI KOGYO SEIYAKU K.K., to carry out this operation in a rotary type concentration crystallizer, respecting the conditions of temperature and of concentration of the medium subjected to crystallization as indicated in this patent application.

These methods do not give entire satisfaction either from the point of view of productivity per unit volume of the equipment or from that of the energy balance.

Now, to face up to the requirements particularly economic which become constantly more severe, Applicants have sought to develop a method and an installation which respond better than those already existing to the various desiderata of practice, in particular precisely from the point of view of the productivity of the crystallization operation per unit volume of the equipment used and the energy balance.

And it is found that this purpose could be achieved by means of a method of continuous crystallization of gluconodeltalactone or GDL, characterized by the fact that a gluconic acid syrup preferably free from crystals and from nuclei, of a richness in gluconic acid higher than 80, preferably higher than 90%, with a concentration of dry matter of 80 to 95%, preferably of 85 to 90% by weight at a temperature of 60° to 85° C., preferably of 65° to 75° C., is introduced into a first crystallization zone of axis preferably substantially vertical which it is led to pass through under stirring and within which it is maintained at a substantially constant temperature, less by 2° to 10° C., preferably by 3° to 5° C. than the saturation temperature, due to which the initiation of crystallization is produced which is manifested by the formation of a mixture of syrup and of crystals of GDL, the average dwell time of a given fraction of mixture inside the zone being from 10 to 30 hours, so that this mixture when emerging from the zone shows a concentration of crystals of 2 to 15%, preferably from to 3 to 10%, said mixture when emerging from the first zone being brought to pass through, from top to bottom, under malaxation, a second crystallization zone of axis preferably substantially vertical, arranged preferably substantially in extension of that of the first zone, a temperature gradient possibly modulated decreasing globally by 0.2° to 1° C./hour, preferably from 0.3° to 0.6° C./hour being imposed inside the second zone on the mixture which passes through it, the said gradient being preferably limited to a first part of the said second zone, this first part extending from the upper end of the second zone to a level of the latter situated between its mid-height and the lower third of its total height, this first part of the second zone being followed by a second part, situated in extension of the first part and playing the role of a ripening zone within which the temperature is maintained constant between 35° and 50° C., preferably between 40° and 45° C., the mixture emerging from the second part of the second zone in the form of a crystalline mass rich in crystals and from which the latter are recovered, the initiation of the crystallization at the level of the first zone being facilitated by the recycling preferably at the level of the upper end of the latter of a fraction of the mixture passing through the second zone, if it exists, through the first part of the second zone, this recycled fraction representing from 10 to 120%, preferably from 40 to 110% and more preferably from 80 to 100% of the amount of syrup introduced into the first zone, this fraction, which is taken up at a level situated in the lower half of the second zone and, if it exists, of the first part of the second zone, being advantageously subjected to a fragmentation of the crystals that it contains before its introduction at the level of the upper end of the first zone.

To carry out the abovesaid method, recourse may be, according to the invention, to an installation comprising essentially two vessels of axis preferably substantially vertical arranged preferably one above the other, the axes of the two vessels being preferably substantially in extension of one another, the first vessel, or crystallization starting vessel, being equipped on one hand with a system for feeding syrup rich in gluconic acid preferably in the vicinity of its upper end, on the other hand with a stirring system of the contents of the vessel and with a system for regulation of the temperature adapted to establish inside the vessel a temperature substantially constant at all points and finally with an extraction system arranged in the vicinity of its lower end, the system being adapted to extract the mixture of syrup and of crystals formed inside the vessel and to conduct this mixture to a point situated in the vicinity of the upper end of the second vessel, or crystallization vessel proper and equipped with a malaxation system for the contents and with a system for regulation of the temperature adapted to establish in the mass subject to crystallization which fills it, a temperature gradient decreasing globally from top to bottom and advantageously limited to a first part of the second vessel, the said first part extending from the upper end of the vessel to a level situated between the mid-height and the lower third of its total height, the said temperature regulating system being then adapted to establish in a second part of this second vessel, a temperature globally constant close to that existing at the level of the lower end of the abovesaid gradient, said second part succeeding downwardly the first part, said second vessel being furthermore equipped, close to its lower end, with a system for extracting continuously a product highly enriched in crystals of GDL which is led by suitable means to a system adapted to recover the GDL crystals from this product, said installation being in addition equipped with a system for recycling to a point situated preferably in the vicinity of the upper end of the first vessel of a part of the contents of the second vessel taken up at a level situated in the lower half of the second vessel and, if it exists, in the lower half of the first part of the second vessel, said recycling system comprising advantageously means for fractionating the crystals contained in the recycled mass.

The invention also aims other features which are preferably used at the same time and which will be more explicitly considered below.

And it will, in any case, be well-understood by means of the additional description which follows and of the accompanying drawing which relate to advantageous embodiments.

The single FIGURE of the drawings shows diagrammatically an installation according to the invention.

Consequently, in order to prepare crystalline gluconodeltalactone according to the invention, procedure is as follows or in equivalent manner.

As raw material a syrup rich in gluconic acid is used, preferably free from crystals and from nuclei, obtained for example, by oxidative fermentation of glucose; this syrup has a content of dry matter of about 80 to 95%, preferably of 85 to 90% by weight, the gluconic acid constituting at least 80% and, preferably, a proportion higher than 90% by weight on the dry matter of this syrup.

This concentrated syrup is led to a first crystallization zone of axis preferably substantially vertical, which it is brought to pass through continuously with stirring and within which it is maintained at a substantially constant temperature less than the saturation temperature, particularly from 2° to 10° C., preferably from 3° to 5° C., due to which the initiation or starting of the crystallization occurs which is manifested by the formation of a mixture of syrup and of crystals of GDL.

The average dwell time of a given fraction of mixture inside this first zone is from 10 to 30 hours, preferbly from 15 to 25 hours, so that the mixture emerging from the vessel has a concentration of crystals of 2 to 15%, preferably from 3 to 10%.

The mixture emerging from the first zone is then brought, to pass through from top to bottom, under malaxation, a second crystallization zone of preferably substantially vertical axis, arranged preferably in extension of that of the first zone.

The temperature of the mixture is maintained, preferably, at the amount of its introduction into the second crystallization zone, at a value close to that which exists within the first zone.

A temperature gradient decreasing globally from top to bottom of 0.2° C. to 1° C./hour, preferably from 0.3° to 0.6° C./hour, is imposed on the mixture, that is to say on the mass subjected to crystallization which traverses this zone; preferably this gradient is limited to a first part of the second crystallization zone; this first part of the second crystallization zone extends from the upper end of the second zone to a level of the latter situated between its mid-height and the lower third of its total height.

The first part of the second zone is followed by a second part situated preferably in extension of the first one and within which the temperature is kept constant, preferably at 35° to 50° C., preferably from 40° to 45° C. This second part plays in fact the role of a ripening zone.

The mixture emerging from this second part is in the form of a crystalline mass rich in GDL crystals, from which the latter are recovered.

The richness of this mass in GDL crystals is from 30 to 60%, preferably from 40 to 55%.

The whole of the mass filling the second crystallization zone, that is to say preferably the first and second parts of the latter, passes through the said zone in the manner of a "piston", term which is used in the technique.

The starting of the crystallization at the level of the first zone is facilitated by the recycling preferably to the level of the upper end of the latter, of a fraction of the mixture passing through the second zone and, if it exists, through the first part of the second zone, this recycled fraction representing from 10 to 120%, preferably from 40 to 110% and more preferably from 80 to 100% of the syrup introduced into the first zone.

This fraction is taken up at a level situated in the lower part of the second zone and, if it exists, of the first part of the second zone; preferably, this level is situated in the lower half of the total height of this first part; this corresponds in practice to recycling a mass whose temperature is about 7.5° to 15° C. lower than that existing in the first zone.

The recycled fraction is in addition subjected, preferably, to a fractionation of the crystals that it contains before its introduction at the level of the upper end of the first zone.

Due to the method according to the invention, there is extracted continuously, in the vicinity of the lower end of the second zone and, if it exists, of the second part of the second or crystallization zone proper, a mass rich in GDL crystals without disturbance of the parameters of the crystallization process occurring, which disturbance would have repercussions at the level of the following separation stage of the liquid phase and of the crystals and which could necessitate intermittent stoppages of the installation. In other words, this method enables a very favourable productivity to be reached per unit volume of the equipment used for the practising of the method. This productivity is higher than that obtained in the methods of the prior art.

The feed flow rate in syrup rich in gluconic acid is selected so that the average dwell time, of a given fraction of the mass subjected to crystallization inside the second crystallization zone is from 40 to 80 hours, preferably from 60 to 70 hours; the value adopted depends on the heat exchange capacities of the means comprised by the second zone and by means of which is established inside said zone, preferably inside a first part of said zone, within the mass subjected to crystallization, the decreasing temperature gradient which has been mentioned above.

Due to the viscosity of the mass subject to crystallization which increases progressively as the proportion of GDL crystals grows, that is to say in the descending direction, the crystallization zone is preferably equipped with driving or suction means suitable for facilitating the progress of the mass inside the zone.

In addition, the means of malaxation and homogeneization comprised by the second crystallization zone must be arranged so that dead zones are avoided and so that heat exchange between the mass subjected to crystallization and the cooling means is as sufficient as possible.

The product extracted from the second crystallization zone and which constitutes, as already indicated, a mass rich in GDL crystals, comprises GDL crystals of a granulometric spectrum characterized by a low proportion of fines and of coarse crystals and hence by a high proportion of crystals of intermediate size, this spectrum not varying over time, due to which the following treatment step, which consists of separating said crystals from the liquid phase in which they are contained, is not disturbed.

This separation comprises a centrifugal draining and possibly washing by means of which the major part of the liquid phase is recovered; the latter forms mother liquors whose concentration of gluconic acid is less than that of the gluconic acid rich starting syrup—this concentration generally reaches from 75 to 98%, preferably from 80 to 92%—and in which almost the whole of the impurities contained in said starting syrup are again found.

Collected mother liquors can be partly recycled and form then part of the constitution of the feeding syrup.

Now, to carry out the method according to the invention, recourse may be had to the installation which will now be discussed.

This installation comprises essentially two vessels 1a and 1b advantageously arranged one (1a) above the other (1b); these vessels have advantageously the shape of cylinders of revolution with axes $X_1$, $Y_1$ and $X_2$, $Y_2$ preferably substantially vertical and preferably situated in extension of one another.

The vessel 1a is equipped
 with a feed system of syrup rich in gluconic acid at the level of its upper end and shown diagrammatically by the pipe 2,
 with a stirring system 3 and
 with a system of regulation of temperature shown diagrammatically at 4 and adapted to establish a temperature constant at all points inside the vessel.

The mixture constituted by gluconic acid syrup and crystals of GDL which is formed inside the vessel 1a flows from the latter at a point 7 situated in the vicinity of the lower end of this vessel; at this point the vessel can comprise a pipe 8 through which the mixture is led to the vessel 1b; it is also possible to provide for the output orifice of the vessel 1a to be arranged facing the input orifice of vessel 1b, the two vessels then being juxtaposed.

As a general rule, it is however the arrangement shown in the FIGURE which is adopted, the two vessels being arranged one beneath the other, preferably in extension of one another, the pipe 8 playing simultaneously the role of extraction pipe for vessel 1a and feed pipe with mixture of gluconic acid syrup and GDL crystals for the vessel 1b at a point 9 of the latter close to its upper end.

The vessel 1b is equipped
 with a system of malaxation and of regulation of temperature which will be discussed and
 with a system of continuous extraction at the level of the lower end of the vessel and shown diagrammatically by pipe 10, the system being adapted to recover the mass rich in GDL crystals obtained at the outlet of vessel 1b.

The system of malaxation and of temperature regulation which is mentioned above may advantageously comprise
 a set of malaxation arms 11 borne at regular intervals by a rotary shaft A whose axis is merged with the axis $X_2Y_2$ of vessel 1b,
 cooling sheets 12 arranged in alternation with the malaxation arms 11 and borne by the wall of vessel 1b, these cooling sheets being traversed by a cooling fluid.

The system of regulation of temperature is arranged so that it permits the establishment inside of vessel 1b, of a temperature gradient globally decreasing from top to bottom.

Preferably, and as contemplated in the disclosed embodiment, the system is adapted in such a way that inside vessel 1b there is established
 a first part $Z_A$ starting from the upper end of the vessel and within which is imposed on the mass contained in the vessel a temperature gradient decreasing globally downwards,
 a second part $Z_B$ situated beneath and in extension of $Z_A$ and within which is imposed on the mass contained in the vessel a temperature substantially constant at all points.

The first part $Z_A$ represents from ½ to ⅔ of the total length of the vessel 1b.

The vessel 1b comprises in addition means shown globally by a pipe 13 comprising a pump 14 and adapted
 to take up at the lower level 15 of the first part $Z_A$ of the vessel, situated in the lower half of the latter, a fraction of the mass M subjected to crystallization and traversing the vessel 1b from top to bottom and
 to recycle this fraction to a level 16 situated in the vicinity of the upper end of the vessel 1a.

Preferably, the pipe 13 comprises fragmentation means 17, for example a grinder, adapted to disaggregate possible aggregates of crystals of gluconic acids contained in the recycled fraction.

For the establishment of the two parts $Z_A$ and $Z_B$, there is made to play a part not only the heat exchange capacity of the temperature regulation system, but also the rotary speed of the malaxation means and the speed with which, under the influence of suction means not shown, the mass subject to crystallization traverses the vessel; in other words, the average dwell time of a given fraction of this mass inside the vessel is made to play a part.

It is pointed out that, in practice, the cooling fluid is water and that the average difference in temperature at a given point of the vessel between this water and the mass subject to crystallization, is of the order of 2° to 10° C.

EXAMPLE (a) Recourse is held to an installation according to the invention comprising two cylindrical vessels 1a and 1b of respective useful volumes of 1 and 3.3 m³.

There is introduced into vessel 1a, with a flow rate of 50 l per hour, a gluconic acid syrup having a content of dry matter of 88% and comprising 92% by weight on dry matter of gluconic acid, the 8% remaining being constituted particularly by other organic acids.

The temperature of the syrup at the input of the vessel 1a is of about 65° C.; it is 61° C. inside the vessel.

The average dwell time inside the vessel 1a of a given fraction of the mixture of syrup and of GDL crystals is of about 20 hours.

At the outlet of the vessel, this mixture shows a concentration of crystals of the order of 7%.

The mixture emerging from the vessel 1a is brought through the pipe 8 to a point 9 of the vessel 1b situated in the vicinity of the upper end of the latter.

Inside the vessel 1b, this mixture is subjected in the part $Z_A$ to a temperature gradient decreasing overall by 0.4° C./hour; the upper temperature of this gradient is 60° C. and the lower temperature, reached at the level of the lower end of the parts $Z_A$ is 45° C.

Inside the part $Z_B$ which forms a continuation of the part $Z_A$, the mixture enriched in GDL crystals is maintained at the temperature of 45° C.

The part $Z_B$ is traversed in about 30 hours.

At the level of point 15 situated at a level of the part $Z_A$ corresponding to 50° C., i.e. corresponding to a level located within the lower third of said vessel, there is taken up from the vessel a fraction of mass subjected to crystallization which passes through it and this fraction is recycled to the upper end of the vessel 1a at 16, after having been submitted to the action of a grinder.

The recycled fraction corresponds to 80% of the amount of syrup introduced through the pipe 2.

The mass rich in GDL crystals extracted at the level of the lower end of the vessel 1b through the pipe 10 is at a temperature close to 45° C. and enables separation of a quantity of crystals corresponding in weight to 43% of the mixture.

Separation of the GDL crystals is done by centrifugal draining, then the crystals are washed.

The content of gluconic acid of the mother liquors thus recovered, after washing, is 86%.

The crystallization yield which is given by the formula:

$$r = \frac{A - H}{100 - H}$$

in which

A, which represents the richness in gluconic acid of the feeding syrup, is 92%,

H, which represents the richness of the mother liquors after washing, is 86%, is 43%.

In this way there are produced daily 658 kg of GDL, which corresponds to a productivity of 200 kg daily and per m³ of the crystallization vessel instead of 130 kg with the conventional method.

In addition, no disturbance requiring stoppage of the installation occurs which operates continuously.

The crystals collected after turbinage and washing show excellent physical and chemical properties.

These crystals are of 99.8% purity, their flow index is good and their granulometric distribution is as follows:

| crystals of size greater than 250 microns | 25% |
|---|---|
| crystals of size comprised between 100 and 350 microns | 92% |

(b) The same equipment and the same operational conditions are used.

However, at a given moment, after having reached the equilibrium of the system, the recycled fraction is taken up at a level situated outside the range according to the invention.

There is then rapidly witnessed a development of the parameters of the crystallization which is manifested after some hours by poor separation at the level of the centrifuges and which finishes by necessitating the stoppage of the installation and the removal of the mass that it contains before starting up again under the conditions according to the invention.

As is self-evident and as emerges besides already from the foregoing, the invention is in no way limited to those of its types of application and embodiments which have been more particularly envisaged; it encompasses, on the contrary, all modifications, particularly that wherein the installation according to the invention comprises a single vessel within which there is materialized by way of appropriate means the starting zone, the crystallization zone proper and the ripening zone, and that wherein the installation according to the invention comprises the vessels for starting crystallization and for crystallization proper as disclosed, the ripening zone being materialized by a third vessel, independent from the two other vessels, located preferably in their extension and comprising means adapted to impose a temperature constant at all points to the mass by which it is traversed and which is coming from the second vessel.

We claim:

1. Method of continuous crystallization of glucono-deltalactone, i.e. GDL, comprising the steps of
    introducing into a first crystallisation zone a gluconic acid syrup of a richness in gluconic acid higher than 80%, of a concentration in dry matter of 80 to 95% by weight and of a temperature of 60° to 85° C.,
    causing said syrup to traverse under stirring said first crystallization zone and maintaining it within said zone at a substantially constant temperature less by 2° to 10° C. than the saturation temperature, due to which the starting of crystallization is produced which is manifested by the formation of a mixture of syrup and of GDL crystals, the average dwell time of a given fraction of the mixture inside the zone being from 10 to 30 hours, so that this mixture emerging from the first zone shows a concentration of crystals of 2 to 15%,
    causing said mixture when emerging from the first zone to pass through, from top to bottom, under malaxation, a second crystallization zone, wherein a temperature gradient decreasing globally from top to bottom by 0.2° to 1° C./hour is imposed on the said mixture,
    taking up at a level situated in the lower half of the second crystallization zone a fraction of the mixture traversing the said second zone, which fraction represents from 10 to 120% of the amount of syrup introduced into the first zone, the average dwell time of a given fraction of the mixture inside the second zone being from 40 to 80 hours,
    recycling said fraction to the level of the upper end of the said first crystallization zone thus facilitating the starting of the crystallization inside the first zone, and
    recovering the crystals from the mixture when emerging from the second zone in the vicinity of its lower end in the form of a crystalline mass rich in crystals.

2. Method according to claim 1, wherein the concentration in dry matter of the gluconic acid syrup introduced into the first crystallization zone is of 85 to 90% by weight.

3. Method according to claim 1, wherein the temperature of the gluconic acid syrup introduced into the first crystallization zone is from 65° to 75° C.

4. Method according to claim 1, wherein the axis of the first crystallization zone is substantially vertical.

5. Method according to claim 1, wherein the gluconic acid syrup is maintained within the first zone at a substantially constant temperature less by 3° to 5° C. than the saturation temperature.

6. Method according to claim 1, wherein the average dwell-time of a given fraction of the mixture of syrup and of GDL crystals inside the first crystallization zone is from 15 to 25 hours.

7. Method according to claim 1, wherein the second crystallization zone has a vertical axis.

8. Method according to claim 1, wherein the temperature gradient imposed inside the second crystallization zone on the mixture which passes through it is non linear.

9. Method according to claim 1, wherein the richness in gluconic acid of the syrup used is higher than 90% by weight.

10. Method according to claim 1, wherein the mixture emerging from the first crystallization zone has a concentration of crystals of 3 to 10% by weight.

11. Method according to claim 1, wherein the temperature gradient is decreasing by 0.3° to 0.6° C./hour.

12. Method according to claim 1, wherein the recycled fraction represents from 40 to 110% of the amount of syrup introduced in the first zone.

13. Method according to claim 1, wherein the recycled fraction represents from 80 to 100% of the amount of syrup introduced in the first zone.

14. Method according to claim 1, wherein the gluconic acid therein employed is free from crystals.

15. Method according to claim 1, wherein the axes of the first and of the second zone are in alignment with each other.

16. Method according to claim 1, wherein the recycled fraction is subjected to fragmentation of the crystals that it contains before its introduction to the level of the upper end of the first zone.

17. Method of continuous crystallization of glucono-deltalactone, i.e. GDL, comprising the steps of
introducing into a first crystallisation zone a gluconic acid syrup of a richness in gluconic acid higher than 80%, of a concentration in dry matter of 80 to 95% by weight and of a temperature of 60° to 85° C.,
causing said syrup to traverse under stirring said first crystallization zone and maintaining it within said zone at a substantially constant temperature less by 2° to 10° C. than the saturation temperature, due to which the starting of crystallization is produced which is manifested by the formation of a mixture of syrup and of GDL crystals, the average dwell time of a given fraction of the mixture inside the zone being from 10 to 30 hours, so that this mixture emerging from the first zone shows a concentration of crystals of 2 to 15%,
causing said mixture when emerging from the first zone to pass through, from top to bottom, under malaxation, a second crystallization zone having an upper and a lower end and comprising a first and a second part, the second part being situated in extension of the first, the first part extending from the upper end to a level of the second zone which is situated between its mid-height and the lower third of its total height, a temperature gradient decreasing by 0.2° to 1° C./hour being imposed to the said mixture inside the first part of the second cristallization zone, the temperature being maintained constant from 35° to 50° C. within the second part of the second cristallization zone, the average dwell time of a given fraction of the mixture inside the zone being from 40 to to 80 hours,
taking up at a level situated within the lower half of the first part of the second crystallization zone a fraction of the mixture traversing the said second zone, which fraction represents from 10 to 120% of the amount of syrup introduced into the first zone,
recycling said fraction to the level of the upper end of the said first crystallization zone thus facilitating the starting of the crystallization inside the first zone, and
recovering the crystals from the mixture when emerging from the second zone in the vicinity of its lower end in the form of a crystalline mass rich in crystals.

18. Method according to claim 17, wherein the temperature within the second part of the second cristallization zone is maintained constant from 40° to 45° C.

19. Method according to the claim 17, wherein the concentration in dry matter of the gluconic acid syrup introduced into the first crystallization zone is of 85 to 90% by weight.

20. Method according to claim 17, wherein the temperature of the gluconic acid syrup introduced into the first crystallization zone is from 65° to 75° C.

21. Method according to claim 17, wherein the axis of the first crystallization zone is substantially vertical.

22. Method according to claim 17, wherein the gluconic acid syrup is maintained within the first zone at a substantially constant temperature less by 3° to 5° C. than the saturation temperature.

23. Method according to claim 17, wherein the average dwell-time of a given fraction of the mixture of syrup and of GDL crystals inside the first crystallizatin zone is from 15 to 25 hours.

24. Method according to claim 17, wherein the second crystallization zone has a vertical axis.

25. Method according to claim 17, wherein the temperature gradient imposed inside the second crystallization zone on the mixture which passes through it is non linear.

26. Method according to claim 17, wherein the richness in gluconic acid of the syrup used is higher than 90% by weight.

27. Method according to claim 17, wherein the mixture emerging from the first crystallization zone has a concentration of crystals of 3 to 10% by weight.

28. Method according to claim 17, wherein the temperature gradient is decreasing by 0.3° to 0.6° C./hour.

29. Method according to claim 17, wherein the recycled fraction represents from 40 to 110% of the amount of syrup introduced in the first zone.

30. Method according to claim 17, wherein the recycled fraction represents from 80 to 100% of the amount of syrup introduced in the first zone.

31. Method according to claim 17, wherein the gluconic acid therein employed is free from crystals.

32. Method according to claim 17, wherein the axes of the first and of the second zone are in alignment with each other.

33. Method according to claim 17, wherein the recycled fraction is subjected to fragmentation of the crystals that it contains before its introduction to the level of the upper end of the first zone.

34. Method of continuous crystallization of glucono-deltalactone, i.e. GDL, according to claim 17, comprising the steps of
introducing into a first crystallisation zone of axis substantially vertical a gluconic acid syrup of a richness in gluconic acid higher than 90%, of a concentration in dry matter of 85 to 90% by weight and of a temperature of 65° to 75° C.,
causing said syrup to traverse under stirring said first crystallization zone and maintaining it within said zone at a substantially constant temperature less by 3° to 5° C. than the saturation temperature, due to which the starting of crystallization is produced which is manifested by the formation of a mixture of syrup and of GDL crystals, the average dwell time of a given fraction of the mixture inside the zone being from 15 to 25 hours, so that this mixture emerging from the first zone shows a concentration of crystals of 2 to 15%, causing said mixture when emerging from the first zone to pass through, from top to bottom, under malaxation, a second crystallization zone of axis substantially vertical, wherein a temperature gradient decreasing of 0.3° to 0.6° C./hour is imposed on the said mixture, the said gradient being limited to a first part of the said second crystallization zone, this first part extending from the upper end of the second zone to a level of the latter situated between its mid-height and the lower third of its total height, this first part of the second zone being followed by a second part situated in extension of the first and within which the temperature is maintained constant from 40° to 45° C., taking up at a level situated in the lower half of the first part of the second crystallization zone a fraction of the mixture traversing the said second zone, which fraction represents from 80 to 100% of the amount of syrup introduced into the first zone, recycling said fraction to the level of the upper end of the said first crystallization zone thus facilitating the starting of the crystallization inside the first zone recovering the crystals from the mixture when emerging from the second zone in the form of a crystalline mass rich in crystals.

* * * * *